(12) United States Patent
Yang et al.

(10) Patent No.: US 12,685,734 B2
(45) Date of Patent: Jul. 21, 2026

(54) N6-METHYLADENOSINE REGULATORS IN UTERINE FIBROIDS

(71) Applicant: The University of Chicago, Chicago, IL (US)

(72) Inventors: Qiwei Yang, Bolingbrook, IL (US); Ayman Al-Hendy, Hinsdale, IL (US)

(73) Assignee: The University of Chicago, Chicago, IL (US)

( * ) Notice: Subject to any disclaimer, the term of this patent is extended or adjusted under 35 U.S.C. 154(b) by 817 days.

(21) Appl. No.: 17/968,386

(22) Filed: Oct. 18, 2022

(65) Prior Publication Data

US 2023/0123265 A1 Apr. 20, 2023

Related U.S. Application Data

(60) Provisional application No. 63/256,847, filed on Oct. 18, 2021.

(51) Int. Cl.
| | |
|---|---|
| *A61K 31/519* | (2006.01) |
| *A61K 35/768* | (2015.01) |
| *A61K 38/44* | (2006.01) |
| *A61K 38/45* | (2006.01) |
| *A61P 35/00* | (2006.01) |
| *C12N 15/113* | (2010.01) |

(52) U.S. Cl.
CPC .......... *A61K 31/519* (2013.01); *A61K 35/768* (2013.01); *A61K 38/44* (2013.01); *A61K 38/45* (2013.01); *A61P 35/00* (2018.01); *C12N 15/1137* (2013.01); *C12N 2310/531* (2013.01)

(58) Field of Classification Search
CPC .................................................. A61K 31/551
USPC ......................................................... 514/220
See application file for complete search history.

(56) References Cited

PUBLICATIONS

Zhang et al (Acta Pharmaceut Sinica B, 2025, 15(3): 1552-1570).*
Yankova et al (Nature, 2021, 593: 597-601).*
Choi et al., "Integrated mutational landscape analysis of uterine leiomyosarcomas," *PNAS*, 118:15, e2025182118, 9 pages, (Apr. 2021).
Krämer et al., "BRD9 Inhibition, Alone or in Combination with Cytostatic Compounds as a Therapeutic Approach in Rhabdoid Tumors," *Int. J. Mal. Sci.*, 18, 1537, 12 pages, (Jul. 2017).
U.S. Appl. No. 17/968,403, filed Oct. 18, 2022.
U.S. Appl. No. 18/345,461, filed Jun. 30, 2023.
Bulun et al., "Uterine Fibroids," *N Engl J Med*, 369: 1344-1355 (Oct. 2013).
Deng et al., "RNA N6-methyladenosine modification in cancers: current status and perspectives," *Cell Res.;* 28(5): 507-517 (May 2018). Published online Apr. 23, 2018.

Dobin et al., "STAR: ultrafast universal RNA-seq aligner," *Bioinformatics*, 29(1): 1-7 (Jan. 2013). Published online Oct. 25, 2012.
Fu et al., "Gene expression regulation mediated through reversible m6A RNA methylation," *Nat Rev Genet.* (5): 293-306 (May 2014). Published online Mar. 25, 2014.
Fujisawa et al., "Functions of bromodomain-containing proteins and their roles in homeostasis and cancer," *Nat Rev Mol Cell Biol*, (18): 246-262 (Apr. 2017). Published online Jan. 5, 2017.
Klionsky et al., "Guidelines for the use and interpretation of assays for monitoring autophagy (4th edition)," *Autophagy*, 17(1): 1-382 (Jan. 2021). Published online Feb. 8, 2021.
Kulikowski et al.,"Inhibitors of bromodomain and extra-terminal proteins for treating multiple human diseases," *Med Res Rev;* 41(1): 223-245. (Jan. 2021) Published online Sep. 14, 2020.
Patel et al. "Alternative therapies in management of leiomyomas," *Fertil Steril;* 102(3): 649-55 (Sep. 2014) Published online Aug. 5, 2014.
Shi et al., "Where, When, and How: Context-Dependent Functions of RNA Methylation Writers, Readers, and Erasers," *Mol Cell.;* 74(4): 640-650, (May 2019), author manuscript as published in PubMed.
Stewart et al., "Carfilzomib, Lenalidomide, and Dexamethasone for Relapsed Multiple Myeloma," *N Engl J Med;* 372: 142-152 (Jan. 2015). Published online Dec. 6, 2014.
Yang et al., "The Mechanism and Function of Epigenetics in Uterine Leiomyoma Development," *Reprod Sci.*, 23(2): 163-75 (Feb. 2016). Published online Apr. 28, 2015.
Yang et al., "Early Life Adverse Environmental Exposures Increase the Risk of Uterine Fibroid Development: Role of Epigenetic Regulation," *Front Pharmacol.*, (7): 1-10 (Mar. 2016).
Yang et al., "The Functional Role and Regulatory Mechanism of Bromodomain- Containing Protein 9 in Human Uterine Leiomyosarcoma," *Cells*, 11(14): 1-22 (Jul. 2022).
Yang et al., "Targeting the Class I Histone Deacetylases in Uterine Leiomysarcoma," *Reproductive Sciences*, 29(1): 232A (Mar. 2022) (1 page) , abstract No. F-102 (1 page).
Yang et al., "Transcriptome Analysis Reveals BRD9 Inhibition-Induced Distinct Pathways in Uterine Fibroids," *Reproductive Sciences*, 29(1): 206A (Mar. 2022), abstract No. F-038, (1 page).
Yang et al., "Targeting Class I Histone Deacetylases in Human Uterine Leiomyosarcoma," *Cells*, 11: 1-27 (Nov. 2022).
Yang et al., "The Functional Role and Regulatory Mechanism of FTO m6A RNA Demethylase in Human Uterine Leiomyosarcom," *International Journal of Molecular Sciences*, 24(9): 1-17 (Apr. 2023).
Yang et al., "Inhibition Of BRD Proteins Suppresses The Phenotype Of Uterine Fibroids Via Regulation Of N6-Methyladenosine Regulators," *Fertil Steril* 116(3): 11 (Oct. 2021), abstract No. O-26 (1 page).
Yang et al., "Inhibition Of BRD Proteins Suppresses The Phenotype Of Uterine Fibroids Via Regulation Of N6-Methyladenosine Regulators," slide presentation associated with *Fertil Steril* 116(3): 11 (Oct. 2021), abstract No. O-26, presentation given Oct. 18, 2021 (15 pages).

(Continued)

*Primary Examiner* — Sean E Aeder
(74) *Attorney, Agent, or Firm* — Leydig, Voit & Mayer, Ltd.

(57) ABSTRACT

In aspects, the present disclosure provides a method of treating or preventing a uterine fibroid in a female mammal, the method comprising, consisting essentially of, or consisting of administering to the female mammal an effective amount of an agent that modulates an N6-methyladenosine (m6A) regulator.

2 Claims, 17 Drawing Sheets

(56)        References Cited

PUBLICATIONS

Yang et al., "Aberrant Expression Of N6-Methyladenosine Regulators In Uterine Fibroids From The Eker Rat Model," *Fertil Steril,* 116(3): e12-e13 (Oct. 2021), abstract No. O-29 (2 pages).

Yang et al., "Aberrant Expression Of N6-Methyladenosine Regulators In Uterine Fibroids From The Eker Rat Model," slide presentation associated with *Fertil Steril,* 116(3): e12-e13 (Oct. 2021), abstract No. O-29, presentation given Oct. 18, 2021 (13 pages).

Yang et al., "The Functional Role and mechanism of Bromodomain-Containing Protein 9 In Human Uterine Leiomyosarcoma," *Fertil Steril,* 24(9): e229 (Oct. 2022), abstract No. P-288 (1 page).

Yang et al., "The Functional Role and mechanism of Bromodomain-Containing Protein 9 In Human Uterine Leiomyosarcoma," poster presentation associated with *Fertil Steril,* 24(9): e229 (Oct. 2022), abstract No. P-288, presentation given Oct. 25, 2022 (11 pages).

Yang et al., "The Regulatory Mechanism Of Histone Deacetylases In Epigenetic Regulation: Emerging Paradigms From Hdac Inhibition Studies In Uterine Leiomyosarcoma," *Fertil Steril,* (118): e338 (Oct. 2022), abstract No. P-543 (1 page).

Yang et al., "The Regulatory Mechanism Of Histone Deacetylases In Epigenetic Regulation: Emerging Paradigms From Hdac Inhibition Studies In Uterine Leiomyosarcoma," poster presentation associated with *Fertil Steril,* (118): e338 (Oct. 2022), abstract No. P-543, presentation given Oct. 26, 2022 (8 pages).

Yang et al., "Bromodomain Containing 9 Regulates Signaling Pathways and Reprograms the Epigenome in Human Uterine Fibroid Cells," Posted date Jul. 18, 2023. (preprint) Preprints (database online), [retrieved on Oct. 4, 2023]. Retrieved from the Internet: <URL: https://www.preprints.org/manuscript/202307.1154/v1> <DOI: https://doi.org/10.20944/preprints202307.1154.v1> (20 pages).

Yang et al., "Pathological reprogramming of epitranscriptomics via METTL3 in Uterine Fibroids," *Reproductive Sciences,* (28)1: 128A-129A (Jul. 2021), abstract No. W-046 (2 pages).

Aicher et al., "Serum response elements activate and cAMP responsive elements inhibit expression of transcription factor Egr-1 in synovial fibroblasts of rheumatoid arthritis patients," International Immunology, 11(1): 47-61 (Sep. 1998) Published online Jan. 1, 1999.

Ali et al., "Activation of β-Catenin Signaling and its Crosstalk With Estrogen and Histone Deacetylases in Human Uterine Fibroids," J Clin Endocrinol. Metab., 105(4): e1517-e1535 (Apr. 2020). Published online Dec. 25, 2019.

Archer et al., "Proteomics, Post-translational Modifications, and Integrative Analyses Reveal Molecular Heterogeneity within Medulloblastoma Subgroups," Cancer Cell, 34: 396-410 and e1-e8 (Sep. 2018).

Belkina et al., "BET Protein Function Is Required for Inflammation: Brd2 Genetic Disruption and BET Inhibitor JQ1 Impair Mouse Macrophage Inflammatory Responses," J. Immunol., 190(7): 3670-3678 (Apr. 2013).

Bell et al., "PIK3CA Cooperates with KRAS to Promote MYC Activity and Tumorigenesis via the Bromodomain Protein BRD9," Cancers, 11(11): 1634, 20 pages (Oct. 2019).

Bertsch et al., "MED12 and HMGA2 mutations: two independent genetic events in uterine leiomyoma and leiomyosarcoma," Modern Pathology, 27:1144-1153 (2014)). Published online Jan. 3, 2014.

Bhargava et al., "IGF2 mRNA binding protein 3 (IMP3) mediated regulation of transcriptome and translatome in glioma cells," Cancer Biology & Therapy, 19(1): 42-52 (Jan. 2018). Published online Dec. 19, 2017.

Bulavin et al., "Loss of Oncogenic H-ras-Induced Cell Cycle Arrest and p38 Mitogen-Activated Protein Kinase Activation by Disruption of Gadd45a," Molecular And Cellular Biology, 23(11): 3859-3871 (Jun. 2003). Published online Mar. 27, 2023.

Carbajo-Garcia, et al., "Integrative analysis of the DNA methylome and transcriptome in uterine leiomyoma shows altered regulation of genes involved in metabolism, proliferation, extracellular matrix, and vesicles," Journal of Pathology, 257: 663-673 (Aug. 2022). Published online Jun. 13, 2022.

Care et al., "Parsimonious Gene Correlation Network Analysis (PGCNA): a tool to define modular gene co-expression for refined molecular stratification in cancer," Systems Biology and Applications, 5(13): 1-17 (Apr. 2019).

Chen et al., "Topoisomerase IIα in Chromosome Instability and Personalized Cancer Therapy," Oncogene, 34(31): 4019-4031 (Jul. 2015), author manuscript as published in PubMed.

Chinenov et al., "Fos-Jun interactions that mediate transcription regulatory specificity," Oncogene, 20(19): 2438-2452. (Apr. 2001).

Choi et al., "Integrated mutational landscape analysis of uterine leiomyosarcomas," PNAS, 118(15): e2025182118, Supplemental Data 14, 2 pages (Apr. 2021).

Choi et al., "Integrated mutational landscape analysis of uterine leiomyosarcomas," PNAS, 118(15): e2025182118, Supplemental Data 15, 2 pages (Apr. 2021).

Conconi et al., "Genomic and Epigenomic Profile of Uterine Smooth Muscle Tumors of Uncertain Malignant Potential (STUMPs) Revealed Similarities and Differences with Leiomyomas and Leiomyosarcomas," Int. J. Mol. Sci., 22(1580): 1-16 (Feb. 2021). Published online Feb. 4, 2021.

Costa et al., "Targeting the PI3K/AKT/mTOR pathway in triple-negative breast cancer: a review," Breast Cancer Res. Treat., 169(3): 397-406. (Jun. 2018). Published online Feb. 7, 2018.

Crawford et al., "Bromodomain 4 activation predicts breast cancer survival," PNAS, 105(17): 6380-6385 (Apr. 2008) Published online Apr. 21, 2008.

D'Angelo et al., "Uterine sarcomas: a review," Gynecologic oncology, 116(1): 131-139 (Jan. 2010). Published online Oct. 23, 2009.

Dawson et al., "Inhibition of BET recruitment to chromatin as an effective treatment for MLL-fusion leukaemia," Nature, 478(7370): 529-533. (Oct. 2011). Published online Oct. 2, 2011, author manuscript as published in PubMed, 12 pages.

De Almeida et al., "Let-7 miRNA's Expression Profile and Its Potential Prognostic Role in Uterine Leiomyosarcoma," Cells, 8, 1452: 1-16 (Nov. 2019). Published online Nov. 17, 2019.

De Carvalho et al., "Treatment with epigenetic agents profoundly inhibits tumor growth in leiomyosarcoma," Oncotarget, 9(27):19379-19395 (Apr. 2018). Published online Apr. 10, 2018.

Del Gaudio et al., "BRD9 binds cell type-specific chromatin regions regulating leukemic cell survival via STAT5 inhibition," Cell Death and Disease, 10(338): 1-14 (Apr. 2019).

Dey et al., "Oncogenic KRAS-Driven Metabolic Reprogramming in Pancreatic Cancer Cells Utilizes Cytokines from the Tumor Microenvironment," Cancer Discovery, 10: 608-625 (Apr. 2020). Published online Feb. 11, 2020.

Di Giorgio et al., "Different class IIa HDACs repressive complexes regulate specific epigenetic responses related to cell survival in leiomyosarcoma cells," Nucleic Acids Research, 48(2): 646-664 (Jan. 2020). Published online Nov. 22, 2019.

Faivre et al., "Selective inhibition of the BD2 bromodomain of BET proteins in prostate cancer," Nature, 578(7794): 306-310 (Feb. 2020). Published online Jan. 22, 2020.

Felix et al., "The etiology of uterine sarcomas: a pooled analysis of the epidemiology of endometrial cancer consortium," Br. J. Cancer, 108(3): 727-734 (Feb. 2013).

Gadducci et al., "Uterine leiomyosarcoma: analysis of treatment failures and survival," Gynecologic oncology, 62(1): 25-32 (Jul. 1996).

Garcia et al., "Evaluation of Hedgehog Pathway Inhibitors as a Therapeutic Option for Uterine Leiomyosarcoma Using the Xenograft Model," Reproductive Sciences, 29: 781-790 (Mar. 2022). Published online Oct. 12, 2021.

Garcia et al., "Targeting Hedgehog Pathway and DNA Methyltransferases in Uterine Leiomyosarcoma Cells," Cells, 10(53): 1-17 (Jan. 2021). Published online Dec. 3, 2020.

Garcia et al., "The Role of Hedgehog Pathway in Female Cancers," Cancer Sci Clin Ther., 4(4): 487-498 (Nov. 2020). Published online Oct. 9, 2020, author manuscript as published in PubMed, 14 pages.

Gazon et al., "Hijacking of the AP-1 Signaling Pathway during Development of ATL," Front. Microbiol., 8: 2686, 13 pages (Jan. 2018).

(56) References Cited

PUBLICATIONS

Gonzalez et al., "Could miRNA Signatures be Useful for Predicting Uterine Sarcoma and Carcinosarcoma Prognosis and Treatment?," Cancers, 10(9): 315, 18 pages (Sep. 2018).

Gothe et al., "Spatial Chromosome Folding and Active Transcription Drive DNA Fragility and Formation of Oncogenic MLL Translocations," Molecular Cell, 75: 267-283 (Jul. 2019). Published online Jun. 12, 2019.

Hana et al., "Uterine sarcomas, insight into its risk factors: A systematic review," Journal of Clinical Oncology, 38 (15), abstract, (2 pages), (May 2020).

Han et al., "N-terminal kinase in rheumatoid arthritis," J. Pharmacol. Exp. Ther., 291(1): 124-30. (Oct. 1999).

Hann et al., "Role of post-translational modifications in regulating c-Myc proteolysis, transcriptional activity and biological function," Semin. Cancer Biol., 16(4): 288-302. (Aug. 2006). Published online Aug. 17, 2006.

Hasan et al., "Epigenetic signatures differentiate uterine and soft tissue Leiomyosarcoma," Oncotarget, 12(16): 1566-1579 (Aug. 2021).

Hemming, et al., "Preclinical Modeling of Leiomyosarcoma Identifies Susceptibility to Transcriptional CDK Inhibitors through Antagonism of E2F-Driven Oncogenic Gene Expression," Clinical Cancer Research, 28(11): 2397-2408 (Jun. 2022), author manuscript as published in PubMed, 26 pages.

Hensley et al., "Fixed-dose rate gemcitabine plus docetaxel as first-line therapy for metastatic uterine leiomyosarcoma: a Gynecologic Oncology Group phase II trial," Gynecol. Oncol., 109(3): 329-334 (Jun. 2008), author manuscript as published in PubMed, 14 pages.

Huang et al., "miR-140-3p functions as a tumor suppressor in squamous cell lung cancer by regulating BRD9," Cancer Lett., 446: 81-89. (Apr. 2019).

Jacomy et al., "ForceAtlas2, a Continuous Graph Layout Algorithm for Handy Network Visualization Designed for the Gephi Software," PLoS ONE, 9(6): 1-12 (Jun. 2014). Published online Jun. 10, 2014.

Jain et al, "Bromodomain Histone Readers and Cancer," J. Mol. Biol., 429(13): 2003-2010 (Jun. 2017).

Jones et al., "Epigenetics in carcinogenesis and cancer prevention," Ann. N.Y. Acad. Sci., 983: 213-9. (Jan. 2006).

Kanwal et al., "Epigenetics and cancer," J. Appl. Physiol., 109: 598-605 (Aug. 2010). Published online Mar. 4, 2010.

Kapoor et al., "BRD9 Inhibition by Natural Polyphenols Targets DNA Damage/Repair and Apoptosis in Human Colon Cancer Cells," Nutrients, 14(4317): 1-9 (Oct. 2022).

Karim et al., "Structural Basis of Inhibitor Selectivity in the BRD7/9 Subfamily of Bromodomains," J. Med. Chem., 63(6): 3227-3237, (Mar. 2020), author manuscript as published in PubMed, 21 pages.

Kato et al., "MYCL is a target of a BET bromodomain inhibitor, JQ1, on growth suppression efficacy in small cell lung cancer cells," Oncotarget, 7(47): 77378-77388 (Nov. 2016). Published online Oct. 14, 2016.

Kaur et al., "Targeting Chromatin Remodeling for Cancer Therapy," Current Molecular Pharmacology, 12: 215-229 (Aug. 2019).

Khare et al., "Epigenetics of colon cancer," Methods Mol Biol., 863: 177-185. (Jan. 2012). Published online Jan. 1, 2012.

Kim et al., "Epigenetics of bladder cancer," Methods Mol Biol., 863: 111-8. (Jan. 2012). Published online Jan. 1, 2012.

Kregel et al., "Functional and Mechanistic Interrogation of BET Bromodomain Degraders for the Treatment of Metastatic Castration-resistant Prostate Cancer," Clin Cancer Res, 25(13): 4038-4048 (Jul. 2019).

Laird et al., "Cancer epigenetics," Human Molecular Genetics, 14(1): 65-76 (Apr. 2005).

Langer et al., "Jun and Fos family protein expression in human breast cancer: correlation of protein expression and clinicopathological parameters," Eur. J. Gynaecol. Oncol., 27(4): 345-352. (Jan. 2006).

Leal et al., "The Bromodomain Inhibitor, INCB057643, Targets Both Cancer Cells and the Tumor Microenvironment in Two Preclinical Models of Pancreatic Cancer," Cancers, 13(1): 1-15 (Dec. 2020).

Lourenco et al., "MYC protein interactors in gene transcription and cancer," Nat Rev Cancer., 21(9): 579-591 (Sep. 2021). Published online Jun. 29, 2021.

Lu et al., "Gene Signature Associated With Bromodomain Genes Predicts the Prognosis of Kidney Renal Clear Cell Carcinoma," Front Genet., 12(643935): 1-12 (Jun. 2021).

Lucas et al., "Targeting the BET family for the treatment of leukemia," Epigenomics, 6(2): 153-155 (Apr. 2014). Published online May 9, 2014.

Magnani et al., "Genome-wide reprogramming of the chromatin landscape underlies endocrine therapy resistance in breast cancer," Proc Natl Acad Sci, 110(16): 1490-1499 (Apr. 2013).

Mason et al., "The BRD9/7 Inhibitor TP-472 Blocks Melanoma Tumor Growth by Suppressing ECM-Mediated Oncogenic Signaling and Inducing Apoptosis," Cancers (Basel), 13(21):1-19 (Nov. 2021).

Mittal et al., "Med12 gain-of-function mutation causes leiomyomas and genomic instability," The Journal of Clinical Investigation, 125(8): 3280-3284 (Aug. 2015).). Published online Jul. 20, 2015.

Moustakim et al., "Chemical probes and inhibitors of bromodomains outside the BET family," Med. Chem. Comm., 7(12): 2246-2264. (Dec. 2016) Published online Sep. 7, 2016.

Nitulescu et al., "The Akt pathway in oncology therapy and beyond (Review)." Int. J. Oncol., 53(6): 2319-2331 (Dec. 2018). Published online Oct. 16, 2018.

Park et al., "Cytotoxic activity of bromodomain inhibitor NVS-CECR2-1 on human cancer cells," Sci Rep., 10(1): 1-15 (Oct. 2020).

Qi et al., "Bromodomain and extraterminal domain inhibitors (BETi) for cancer therapy: chemical modulation of chromatin structure," Cold Spring Harbor Perspect. Biol., 6(12): 1-3 (Dec. 2014).

Qiu et al., "JQ1 suppresses tumor growth through downregulating LDHA in ovarian cancer," Oncotarget, 6(9): 6915-6930. (Mar. 2015). Published online Feb. 5, 2015.

Reynolds et al., "A View on Drug Development for Cancer Prevention," Cancer Discovery, 13(5): 1058-1083, (May 2023).

Richter et al., "Combined Inhibition of Epigenetic Readers and Transcription Initiation Targets the EWS-ETS Transcriptional Program in Ewing Sarcoma," Cancers (Basel), 12(2): 1-17(Jan. 2020).

Santillan et al., "Bromodomain and histone acetyltransferase domain specificities control mixed lineage leukemia phenotype," Cancer Res., 66(20):10032-10039. (Oct. 2006).

Schrump et al."Utilization of chromatin remodeling agents for lung cancer therapy," Cancer J., 13(1): 56-64. (Jan. 2007).

Seagle et al., "Prognosis and treatment of uterine leiomyosarcoma: A National Cancer Database study," Gynecologic oncology, 145(1): 61-70. (Apr. 2017) Published online Mar. 15, 2017.

Shi et al., "Loss of TRIM33 casues resistance to BET bromodomain inhibitors through MYC-and TGF-β-dependent mechanisms," PNAS, 113 (31): E4558-E4566, (Jul. 2016).

Shi et al., "Loss of TRIM33 casues resistance to BET bromodomain inhibitors through MYC-and TGF-β-dependent mechanisms," PNAS, 113 (31): Supporting Information, 8 pages, (Jul. 2016).

Sima et al., "The genetic alteration spectrum of the SWI/SNF complex: The oncogenic roles of BRD9 and ACTL6A," PLoS ONE, 14(9): e0222305 (14 pages), (Sep. 2019).

Sparic, et al., "Molecular Insights in Uterine Leiomyosarcoma: A Systematic Review," International Journal of Molecular Sciences, 23(9728): 1-14 (Aug. 2022).

Supek et al., "REVIGO summarizes and visualizes long lists of gene ontology terms.," PLoS One, 6(7): 1-9 (Jul. 2011).

The Oxford English Dictionary, definition of "prevent," [retrieved Feb. 1, 2024], (2 pages).

Tsai et al., "Histone deacetylase interacts directly with DNA topoisomerase II," Nat Genet., 26(3): 349-553. (Nov. 2000).

Tu et al., "Myc and its interactors take shape," Biochim. Biophys. Acta., 1849(5): 469-483. (May 2015). Published online Jun. 14, 2014.

Wang et al., "The Role of the Transcription Factor EGR1 in Cancer," Front. Oncol., 11(642547):1-10 (Mar. 2021).

(56) References Cited

PUBLICATIONS

Wong et al., "Interplay between epigenetics and metabolism in oncogenesis: mechanisms and therapeutic approaches," Oncogene, 36(24):3359-3374. (Jan. 2017).

Xie et al., "Gene Set Knowledge Discovery with Enrichr," Curr. Protoc., 1(3): 1-84 (Mar. 2021), author manuscript as published in PubMed, 84 pages.

Yamaguchi et al., "Case of leiomyosarcoma arising from subserosal leiomyoma," J. Obstet. Gynaecol. Res., 45(9): 1944-7. (Jun. 2019).

Yang et al., "Comprehensive Review of Uterine Fibroids: Developmental Origin, Pathogenesis, and Treatment," Endocrine Reviews, 43(4):678-719 (Nov. 2021).

Yang et al., "Altered DNA repair genes in human uterine fibroids are epigenetically regulated via EZH2 histone methyltransferase," Fertility and Sterility, 104(3): Supplement E72 (Oct. 2015).

Yang et al., "Epigenetic alterations differ in phenotypically distinct human neuroblastoma cell lines," BMC Cancer, 10(286): 1-10 (Jun. 2010).

Yang et al., "Association of epigenetic inactivation of RASSF1A with poor outcome in human neuroblastoma," Clin Cancer Res., 10(24): 8493-8500. (Dec. 2004).

Yang et al., "Methylation-associated silencing of the thrombospondin-1 gene in human neuroblastoma," Cancer Res., 63(19):6299-310. (Oct. 2003).

Yang et al., "Bromodomain-Containing 9 Regulates Signaling Pathways and Reprograms the Epigenome in Immortalized Human Uterine Fibroid Cells," International Journal of Molecular Sciences, 25(95): 1-21 (Jan. 2024).

Ying et al., "CDK1 serves as a novel therapeutic target for endometrioid endometrial cancer," J Cancer, 12(8): 2206-2215 (Feb. 2021) Published online Feb. 22, 2021.

Zhang et al., "Aberrant activation of m6A demethylase FTO renders HIF2alpha(low/-) clear cell renal cell carcinoma sensitive to BRD9 inhibitors," Sci. Transl. Med., 13(613): 1-15 (Sep. 2021).

Zhang et al., "The aberrant upstream pathway regulations of CDK1 protein were implicated in the proliferation and apoptosis of ovarian cancer cells," J. Ovarian Res., 10(1): 1-11 (Sep. 2017).

Zhao et al., "Investigating crosstalk between H3K27 acetylation and H3K4 trimethylation in CRISPR/dCas-based epigenome editing and gene activation," Sci Rep., 11(1):1-11 (Aug. 2021).

Zhu et al., "Targeting BRD9 for Cancer Treatment: A New Strategy," Onco. Targets Ther., 13: 13191-13200. (Dec. 2020).

Zuccala et al., Misdirecting methylation to drive oncogenesis, Nat. Rev. Cancer, 16(7): 410 (Jun. 2016).

* cited by examiner

STM2457

Fig. 8B

DAC51

Fig. 8A

N6-METHYLADENOSINE REGULATORS IN UTERINE FIBROIDS

CROSS-REFERENCE TO RELATED APPLICATION

This patent application claims the benefit of U.S. Provisional Patent Application No. 63/256,847, filed Oct. 18, 2021, which is incorporated by reference herein in its entirety.

STATEMENT REGARDING FEDERALLY SPONSORED RESEARCH OR DEVELOPMENT

This invention was made with Government support under Grant Numbers HD106285 awarded by the National Institutes of Health. The Government has certain rights in this invention.

BACKGROUND

Uterine fibroids (UFs) are benign smooth muscle tumors that are a major cause of gynecologic dysfunction, such as menometrorrhagia and anemia, pelvic pressure and bulk symptoms, infertility, recurrent miscarriage, and preterm labor. UFs are the most common pelvic tumor, occurring in 80% of women. Uterine fibroids exhibit an extraordinary range of clinical presentations with lesions that routinely range from 5 mm to over 25 cm in size.

There is an ongoing need in the art to treat UFs.

BRIEF SUMMARY

In aspects, the present disclosure provides a method of treating or preventing a uterine fibroid in a female mammal, the method comprising, consisting essentially of, or consisting of administering to the female mammal an effective amount of an agent that modulates an N6-methyladenosine (m6A) regulator.

Additional aspects of the present disclosure are as described herein.

BRIEF DESCRIPTION OF THE DRAWINGS

FIGS. 8A-8B are illustrations of the chemical structures of the m6A inhibitors DAC51 (FIG. 8A) and STM2457 (FIG. 8B).

DETAILED DESCRIPTION

Figure 1:
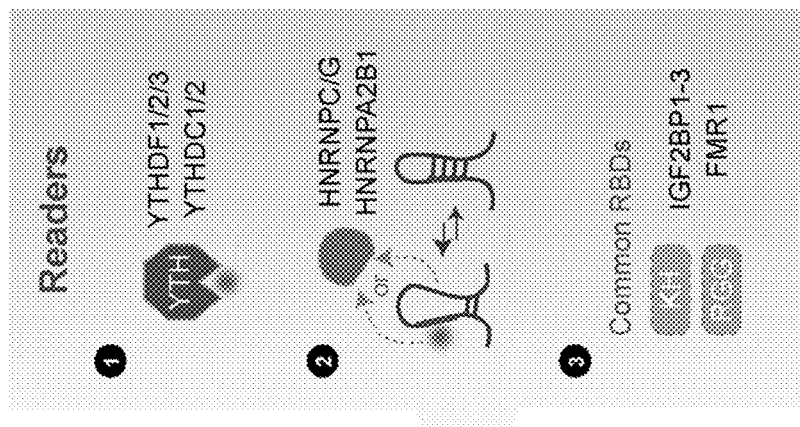
FIG. 1 is a diagram that illustrates the N6-methyladenosine (m6A) pathway in the epitranscriptome.
Figure 1:
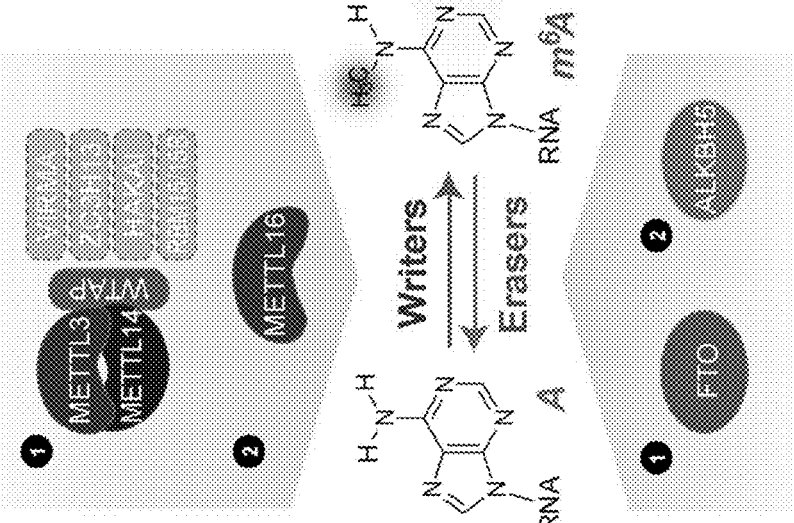

In aspects, the present disclosure provides a method of treating or preventing a uterine fibroid in a female mammal, the method comprising, consisting essentially of, or consisting of administering to the female mammal an effective amount of an agent that modulates an N6-methyladenosine (m6A) regulator.

As used herein, a "uterine fibroid" (UF), is a benign tumor of the uterus that consists of a mass or population of smooth muscle cells and connective tissue that grows, usually slowly, within the uterine wall. Epidemiologic studies demonstrate that UFs, also known as leiomyomas, initially form after menarche. It is suspected that fibroid growth is due to a monoclonal, deregulated proliferation of uterine smooth muscle myometrial cells. The primary tumor cell type resulting from the growth of the fibroid are derived from myometrial cells.

UFs have a high accumulative incidence. UFs are one of the most common tumors. Complications arising from uterine fibroids account for approximately a third of all hysterectomies performed in the U.S., and are associated with high morbidity from uterine bleeding and pain. By age 50 approximately 75% of women have developed UFs. A significant number of those with UFs suffer from debilitating pelvic pain, heavy and prolonged bleeding, which may lead to anemia and iron deficiency, bowel and bladder dysfunction, and infertility. UFs also cause symptoms such as low back pain, urinary frequency and urgency, pain during intercourse (dyspareunia), can cause pre-term labor, and have a negative impact on fertility (due to cavity distension, and alteration of endometrial receptivity and sexual function).

The terms "treat," "treating," "treatment," "therapeutically effective," etc. used herein do not necessarily imply 100% or complete treatment, etc. Rather, there are varying degrees, which one of ordinary skill in the art recognizes as having a potential benefit or therapeutic effect. In this respect, the agent that modulates an m6A regulator and methods can provide any amount of any level of treatment. Furthermore, the treatment provided by the disclosed method can include the treatment of one or more conditions or symptoms of the disease or condition being treated.

The disclosed methods comprise using an effective amount of an agent that modulates an m6A regulator. An "effective amount" means an amount sufficient to show a meaningful benefit. A meaningful benefit includes, for example, detectably treating, relieving, or lessening one or more symptoms of UFs; inhibiting, arresting development, preventing, or halting further development of UFs; reducing the size and/or mass of UFs; reducing the severity of UFs; preventing UFs from occurring in a subject at risk thereof but yet to be diagnosed. The meaningful benefit observed can be to any suitable degree (10%, 20%, 30%, 40%, 50%, 60%, 70%, 80%, 90% or more). In aspects, one or more symptoms are prevented, reduced, halted, or eliminated subsequent to administration of an agent that modulates an m6A regulator as described herein, thereby effectively treating the disease to at least some degree.

One skilled in the art will recognize that dosage will depend upon a variety of factors, including the age, condition or disease state, predisposition to disease, genetic defect or defects, and body weight of the subject. The size of the dose will also be determined by the route, timing and frequency of administration as well as the existence, nature, and extent of any adverse side-effects that might accompany the administration of a particular active agent and the desired effect. It will be appreciated by one of skill in the art that various conditions or disease states may require prolonged treatment involving multiple administrations.

The mammal may be any suitable mammal. Mammals include, but are not limited to, the order Rodentia, such as mice, and the order Lagomorpha, such as rabbits. The mammal can be from the order Carnivora, including Felines (cats) and Canines (dogs). The mammal can be from the order Artiodactyla, including Bovines (cows) and Swines (pigs) or of the order Perissodactyla, including Equines (horses). The mammal can be of the order Primates, Cebids, or Simioids (monkeys) or of the order Anthropoids (humans and apes). In aspects, the mammal is human.

The epitranscriptome includes all the biochemical modifications of the RNA within a cell. Among these post-transcriptional RNA modifications, m6A is the abundant, dynamic, and reversible modification involved in many biological events and diseases.

As used herein, the term "m6A regulator" is any molecule that regulates m6A modifications to RNA. Without wishing to be bound by theory, m6A regulators can be further categorized as "erasers," "readers," and "writers." As used herein, an "eraser" is defined as a category of enzymes that demethylate m6A. m6A erasers include fat mass and obesity-associated protein (FTO) and human AlkB homolog 5 (ALKBH5). As used herein, a "reader" is defined as a protein that recognizes and binds to m6A. m6A readers include YT521-B homology domain containing proteins (YTHDC) such as YTHDC1 and YTHDC2, YT521-B homology domain N6-methyladenosine RNA binding proteins (YTHDF) such as YTHDF1, YTHDF2, and YTHDF3, eukaryotic initiation factor 3 (eIF3), fragile X messenger riboprotein 1 (FMR1), heterogeneous nuclear ribonucleo-proteins (HNRNPs) such as HNRNPC, HNRNPG, and HNRNPA2B1, and insulin-like growth factor 2 mRNA-binding proteins (IGF2BP) such as IGF2BP1, IGF2BP2, and IGF2BP3. As used herein, a "writer" is defined as an m6A methyltransferase complex that post-transcriptionally adds the m6A mark. The m6A methyltransferase complex include core subunits such as methyltransferase-like 3 (METTL3), which catalyzes the methyl transfer, and methyltransferase-like 14 (METTL14), which also methylates adenosine residues at the N(6) position of some mRNAs. The m6A methyltransferase complex also includes adaptor subunits such as RNA binding motif protein 15 (RBM15), Wilms' tumor 1-associating protein (WTAP), vir-like m6A methyltransferase associated (VIRMA), E3 ubiquitin-protein ligase Hakai (HAKAI), also known as casitas B-lineage lymphoma-transforming sequence-like protein 1 (CBLL1), and zinc finger CCCH-type containing protein 13 (ZC3H13). These adaptors play an important role in targeting the "writers" to distinct sets of genes in the chromatin, resulting in transcript-specific m6A methylation.

In aspects the agent that modulates an m6A regulator is an antibody. In aspect the agent is a lentivirus. Examples of lentiviruses that modulate an m6A regulator include, but are not limited to: the shMETTL3 lentivirus from Origene that inhibits through knockdown METTL3. The amount (e.g., therapeutically effective amount) of a lentivirus that modulates an m6A regulator suitable for administration depends on, e.g., the particular route of administration and the weight of the mammal to be treated. Several doses can be provided over a period of days. In aspects the agent that modulates an m6A regulator is the shMETTL3 lentivirus.

In aspects the agent that modulates an m6A regulator is a m6A inhibitor such as, but not limited to: inhibitory RNAs (RNA interference), the FTO inhibitor DAC51, and the METTL3 inhibitor STM2457. The amount (e.g., therapeutically effective amount) of an m6A inhibitor that modulates an m6A regulator suitable for administration depends on, e.g., the particular route of administration and the weight of the mammal to be treated. Several doses can be provided over a period of days. In aspects the agent that modulates an m6A regulator is the METTL3 inhibitor STM2457.

In aspects the m6A regulator is an m6A writer. Examples of m6A writers include, but are not limited to: METTL3, METTL14, RBM15, WTAP, VIRMA, HAKAI, also known as, CBLL1, and ZC3H13.

In aspects the m6a regulator is the m6A writer METTL3. In aspects the agent that modulates the m6A regulator is a lentivirus and the m6A regulator is METTL3. The amount (e.g., therapeutically effective amount) of a lentivirus that modulates METTL3 suitable for administration depends on, e.g., the particular route of administration and the weight of the mammal to be treated. In aspects, the amount of lentivirus that modulates an m6A regulator can be 50 multiplicity of infection (MOI). Several doses can be provided over a period of days.

In aspects the m6a regulator is an m6A eraser. Examples of m6A erasers include, but are not limited to: FTO and ALKBH5. In aspects the m6A eraser is FTO.

The following includes certain aspects of the disclosure.

1. A method of treating or preventing a uterine fibroid in a female mammal, the method comprising administering to the female mammal an effective amount of an agent that modulates an N6-methyladenosine (m6A) regulator.

<div align="center">5</div>

2. The method of aspect 1, wherein the agent is an antibody.

3. The method of aspect 1, wherein the agent is a lentivirus.

4. The method of aspect 1, wherein the agent is STM2457.

5. The method of aspect 1, wherein the m6A regulator is an m6A writer.

6. The method of aspect 5, wherein the m6A writer is methyltransferase-like 3 (METTL3).

7. The method of aspect 2, wherein the m6A regulator is an m6A writer.

8. The method of aspect 7, wherein the m6A writer is methyltransferase-like 3 (METTL3).

9. The method of aspect 3, wherein the m6A regulator is an m6A writer.

10. The method of aspect 9, wherein the m6A writer is methyltransferase-like 3 (METTL3).

11. The method of aspect 10, wherein the lentivirus knocks down the METTL3.

12. The method of aspect 1, wherein the lentivirus is the shMETTL3 lentivirus.

13. The method of aspect 1, wherein the m6A regulator is an m6A eraser.

14. The method of aspect 13, wherein the m6A eraser is fat mass and obesity-associated protein (FTO).

15. The method of aspect 2, wherein the m6A regulator is an m6A eraser.

16. The method of aspect 15, wherein the m6A eraser is fat mass and obesity-associated protein (FTO).

17. The method of aspect 3, wherein the m6A regulator is an m6A eraser.

18. The method of aspect 17, wherein the m6A eraser is fat mass and obesity-associated protein (FTO).

It shall be noted that the preceding are merely examples of aspects of the disclosure. Other exemplary aspects are apparent from the entirety of the description herein. It will also be understood by one of ordinary skill in the art that each of these aspects may be used in various combinations with the other aspects provided herein.

The following examples further illustrate aspects of the disclosure, but, of course, should not be construed as in any way limiting its scope.

<div align="center">Example 1</div>

This example demonstrates aberrant expression of m6A regulators and their role in human UFs.

<div align="center">Materials and Methods</div>

UF Tissue Sample Collection

The UF tissues were obtained from the University of Chicago Tissue Bank.

Approval from the Institutional Review Board (#20-1414) at the University of Chicago was obtained for the retrospective chart review of UF patients. Informed consent was obtained from all the patients participating in the study before surgery. The cases with an initial diagnosis of UF at University of Chicago Hospital were reviewed, and the diagnosis was confirmed by H&E evaluation and immunohistochemistry. A total of nine cases with UFs were used and human UFs (n=22) and matched myometrium tissue (n=7) were collected at the time of hysterectomy.

Western Immunoblot

Cells were collected and lysed in RIPA lysis buffer with protease and phosphatase inhibitor cocktail (Thermo Scientific, Waltham, MA, USA), and the protein was quantified <div align="center">6</div> using the Bradford method (Bio-Rad Protein Assay kit). The antibodies used were METTL3 (ab195352, Abcam), YTHDC1 (ab122340, Abcam), YTHDC2 (35440, Cell Signaling), YTHDF2 (ab220163, Abcam), BCL-2 (ab182858, Abcam), FN (26836, Cell Signaling), PCNA (GTX100539, Genetex). The antigen-antibody complex was detected with Trident Femto Western HRP substrate (GeneTex, Irvine, CA, USA). Specific protein bands were visualized using ChemiDoc XRS p molecular imager (Bio-Rad, Hercules, CA, USA).

Cell Culture

The immortalized human leiomyoma cell line (HuLM) and immortalized human uterine smooth muscle cell line (UTSM) were cultured and maintained in phenol red-free, Dulbecco's Modified Eagle Medium: Nutrient Mixture F-12. The cells were grown at 37° C. and 5% $CO_2$ in an incubator with saturating humidity.

shRNA Knockdown of METTL3

METTL3 knockdown was performed in HuLM cells using shRNA delivered by lentivirus (Origene) to determine its role in uterine fibroids. The control group used scrambled shRNA (Origene). The HuLM cells were seeded in 12-well-dish ($2.5 \times 10^5$ cells per well), and then incubate 18-20 hours at 37° C. in a humidified 5% $CO_2$ incubator. The medium was removed, and a new medium with 50 MOI lentiviral particles and polybrene (8 ug/ml) was added. After 18-20 hours of culture, the medium was replaced with fresh pre-warmed complete culture medium. After 2 days, the cells were subjected to puromycin selection to obtain stable METTL13 knockdown cells.

Cell Proliferation Assay

Cell proliferation was measured using a 3-(4,5-dimethyl-thiazol-2-yl)-2,5-diphenyltetrazolium bromide (MTT) assay. $4 \times 10^4$ HuLM cells treated with scrambled shRNA or METTL3 shRNA per well were seeded into 12-well tissue culture plates with either vehicle (DMSO) or staurosporine (0.1 μM for 24 hours). This assay was performed three times in triplicate.

Quantitative Real Time PCR Analysis

Total RNA was isolated using Trizol reagent (Invitrogen, California USA). The concentration of total RNA was determined using NanoDrop (Thermo Scientific, Waltham, MA). One microgram of total RNA from each sample was reverse transcribed to complementary DNA (cDNA) using the High-Capacity cDNA Transcription Kit (Thermo Scientific, Waltham, MA). Quantitative real-time polymerase chain reaction (qRT-PCR) was performed to determine the messenger RNA (mRNA) expression of eight m6A regulators: writers (METTL3, METTL14), readers (YTHDC1,2; YTHDF1,2), and erasers (FTO, ALKBH5) in UF and matching MyoF tissue from Eker rats. The real-time PCR reactions were performed using CFX96 PCR instrument using SYBR Green Supermix (Bio-Rad, Hercules, California, USA). 18S was used as an internal control. The results are presented as relative gene expression using CFX Maestro™. The assay was performed three times in triplicate.

Statistical Analysis

All experiments were conducted with at least three biological replicates. Comparisons between groups were made using student t-tests.

<div align="center">Results</div>

Expression of m6A Regulators and their Role in Human UFs

Figure 2A:
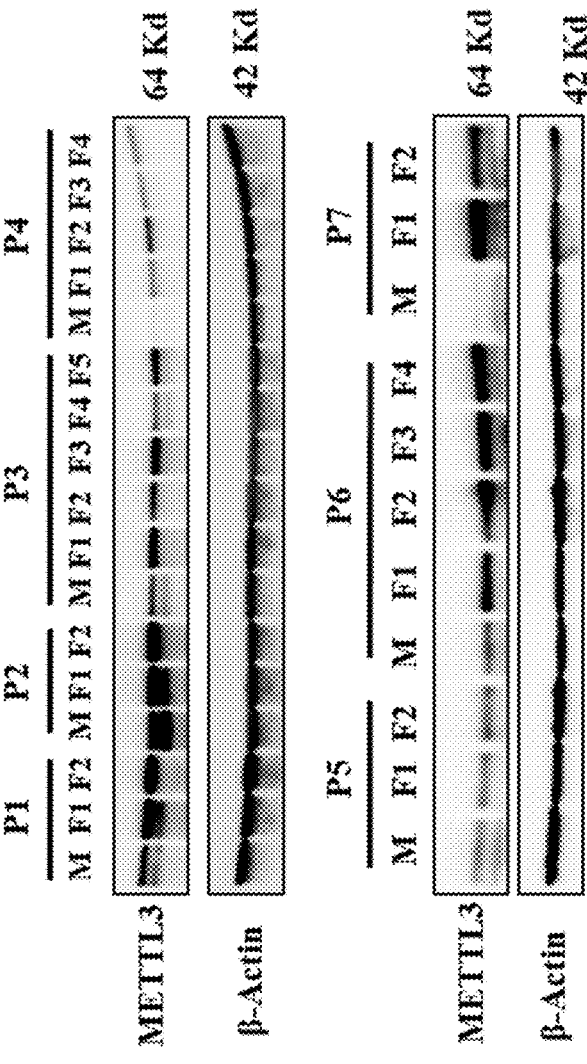
FIGS. 2A-2B are a Western blot image of methyltransferase-like protein 3 (METTL3) and β actin levels in UFs and myometrium from fibroid containing uterus (MyoF) of humans (FIG. 2A) and an immunoblot analysis dot graph of the fold change in UF over MyoF of METTL3 levels (FIG. 2B). P indicates the patient (n=7), M indicates the MyoF tissue (n=7), F indicates the UFs (n=22).
Figure 2B:
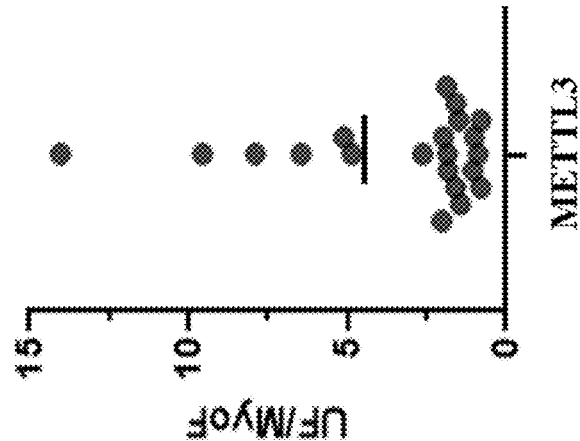
Figure 3A:
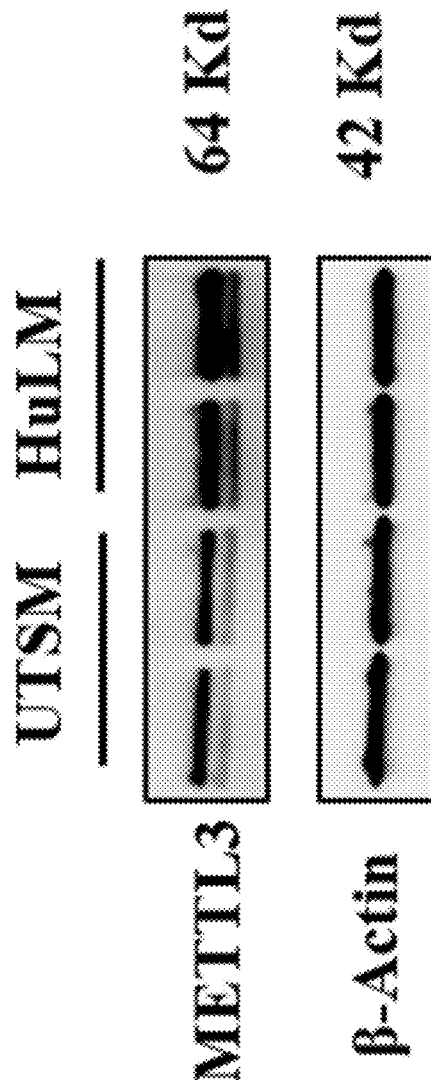
FIGS. 3A-3F are a Western blot image of METTL3 and β actin levels in immortalized human uterine leiomyoma (HuLM) cells and immortalized uterine smooth muscle (UTSM) cells (FIG. 3A), a Western blot image of METTL3 and β actin levels in HuLM cells treated with scrambled or METTL3 shRNA (FIG. 3B), an immunoblot analysis dot graph of the fold change of METTL3 over actin in the scramble and METTL3 shRNA treated HuLM cells (FIG. 3C), a Western blot image of Bax, Bcl2, and β actin levels in HuLM cells treated with scrambled or METTL3 shRNA (FIG. 3D), an immunoblot analysis dot graph of the fold change in BAX and Bcl2 over β actin in HuLM cells treated with METTL3 shRNA (FIG. 3E), and a cell proliferation analysis bar graph showing the relative proliferation of HuLM cells treated with scrambled control shRNA (CTL) and METTL3 shRNA (KD) when cultured in the presence of a vehicle control (VEH) or Staurosporine (STS) (FIG. 3F).
Figure 3B:
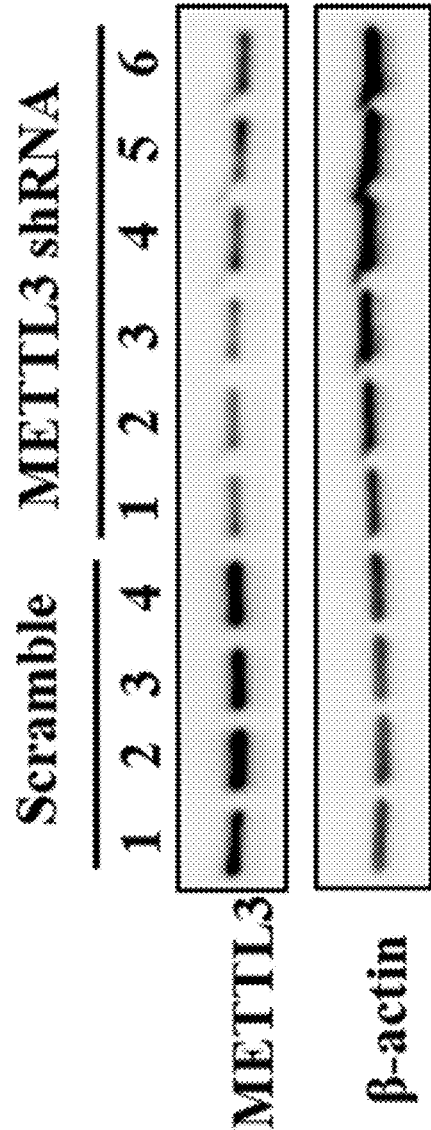
Figure 3C:
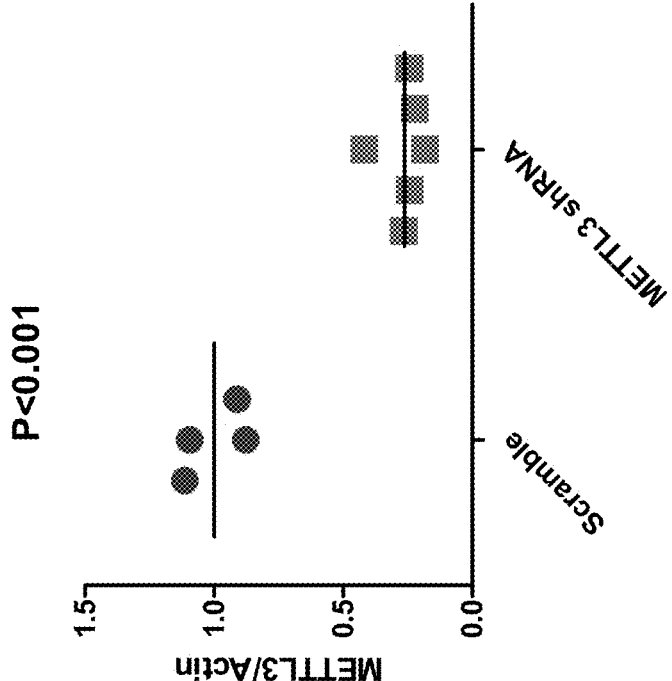
Figure 3D:
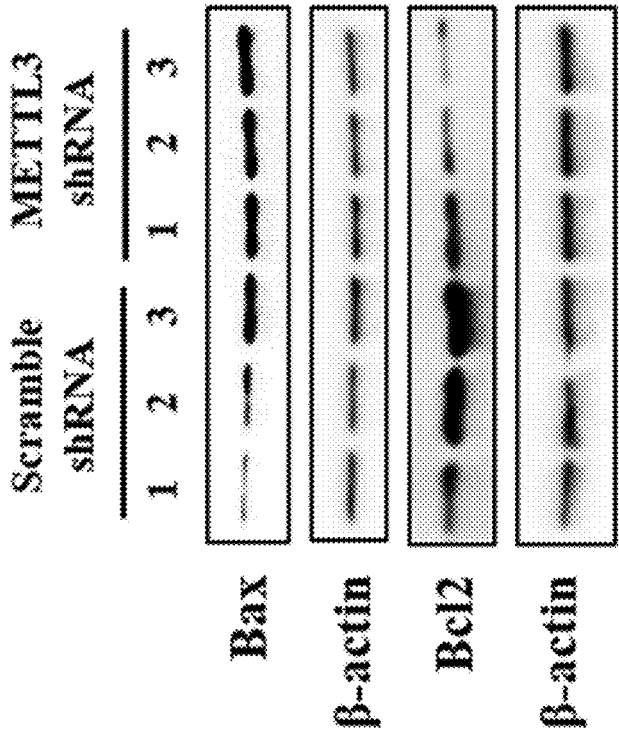
Figure 3E:
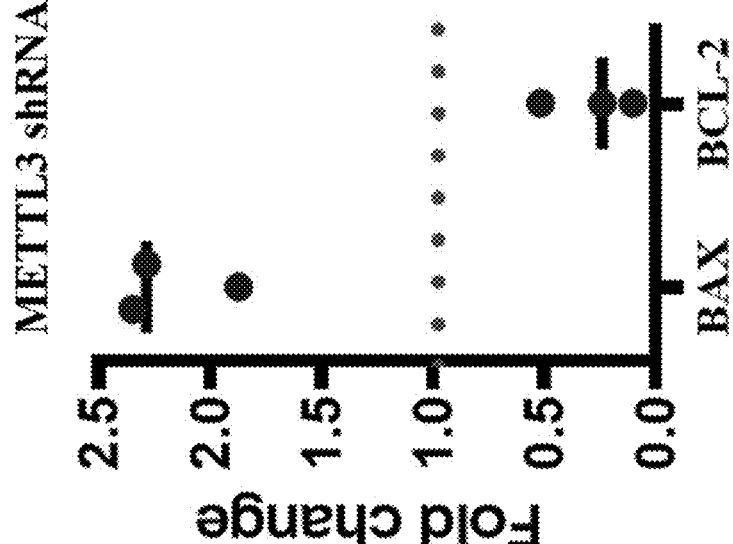
Figure 3F:
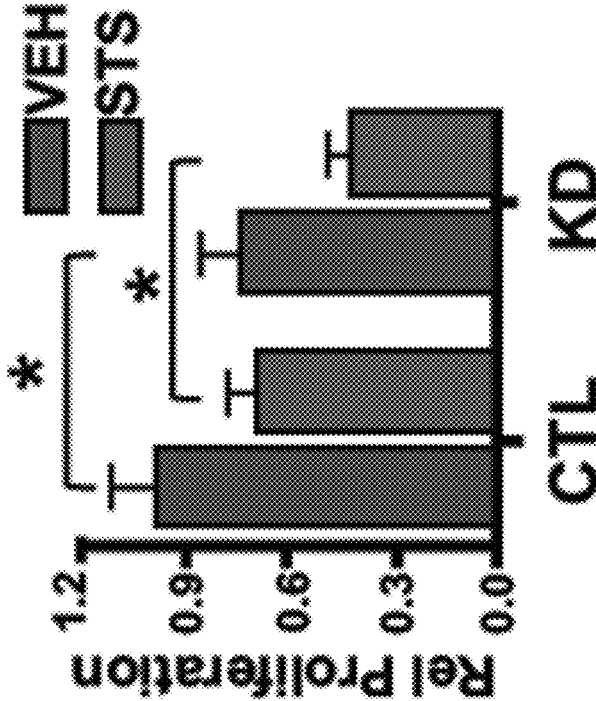

Human UFs (n=22) and matched myometrium tissue (n=7) were collected at the time of hysterectomy from seven patients. Immunoblot analysis was performed on human uterine fibroids (n=22) and matching myometrium tissue (n=7) to determine METTL3 protein levels, using β Actin as a control. The student's t-test was used to determine the significant differences. The N6-methyladenosine writer METTL3 is significantly upregulated in UFs as compared to patient-matched myometrium as shown in FIGS. 2A-B. The METTL3 expression is also upregulated in cells from a uterine fibroid cell line (HuLM) as compared to those from a myometrial cell line (UTSM) as shown in FIG. 3A. METTL3 Knockdown using shRNA significantly down-regulates METTL3 expression compared to scrambled shRNA controls, as shown in FIGS. 3B-C. Knockdown of METTL3 decreased the expression of BCL2, which plays a role in promoting cell survival and inhibiting the actions of pro-apoptotic proteins, as shown in FIGS. 3D-E. In addition, the knockdown of METTL3 increased the expression of BCL-2-associated X protein (BAX), a pro-apoptotic member of the BCL-2 family of genes, as shown in FIGS. 3D-E. Moreover, METTL3-knockdown cells, compared to control-knockdown cells, were characterized by significantly reduced proliferation and enhanced sensitivity to the apoptosis-inducing agent staurosporine, as shown in FIG. 3F.

Figure 4A:
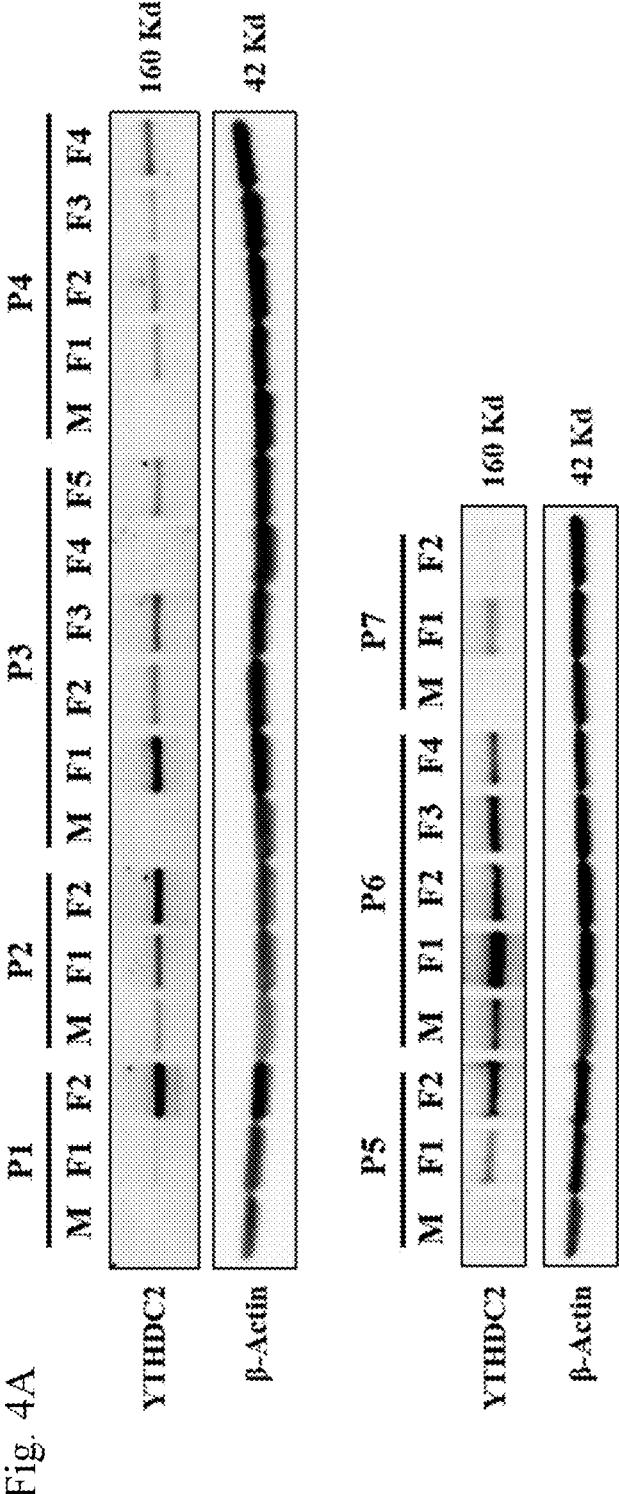
FIGS. 4A-4B are a Western blot image of YT521-B homology domain containing protein 2 (YTHDC2) and β actin levels in UFs and MyoF tissue of humans (FIG. 4A) and an immunoblot analysis dot graph of the fold change in UF over MyoF of YTHDC2 levels (FIG. 4B). P indicates the patient (n=7), M indicates the MyoF tissue (n=7), F indicates the UFs (n=22).
Figure 4B:
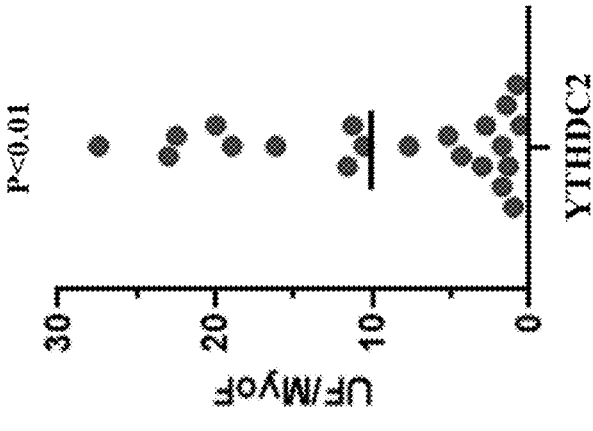

Additional immunoblot analysis was performed in the same manner to determine the levels of YTHDC2 protein, a key reader in human UFs and myometrium tissues, as shown in FIG. 4A. The protein levels of YTHDC2 were significantly unregulated in human UFs compared to patient-matched MyoF, as shown in FIG. 4B.

These results demonstrate that m6A writer METTL3 protein is aberrantly expressed in human UFs. In addition to METTL3, other m6A regulators, such as YTHDC2, are also dysregulated in human UFs compared to matched MyoF tissue. Knockdown of METTL3 induces apoptosis in UF cells. UFs that have knocked down METTL3 levels are sensitive to apoptosis inducers, such as staurosporine, compared to surrounding myometrium.

Example 2

This example demonstrates UF development in Eker rats correlates with human UFs.

Materials and Methods

Eker Rat Husbandry

Female Eker rats [Long Evans; Tsc-2(Ek/+)] were obtained from an in-house Eker rat colony. All experiments using these animals were conducted in accordance with guidelines and provisions issued by the National Institutes of Health. Female Eker rats were raised to late adult stage, age 11-15 months. These rats were treated with hormones to induce UFs.

TABLE 1

|  | Rat | Human |
| --- | --- | --- |
| Presentation | High frequency (~65%) often multiple, | High frequency often multiple, |
|  | Histologically, primarily epithelioid, also typical and mixed | Histologically, typical well-differentiated smooth muscle, also epithelioid |
|  | Benign | Benign |
|  | Leiomyosarcoma very infrequent | Leiomyosarcoma very rare |
| Hormone Responsiveness | Hormone-dependent Expression of ER, PR Response to SERMs | Hormone-dependent Expression of ER, PR Response to GnRH agonists |

TABLE 1-continued

|  | Rat | Human |
| --- | --- | --- |
| Molecular Alterations | Pregnancy protective TSC2 | Pregnancy protective MED12 |
|  | No specific chromosome aberrations | Characteristic translocation |
|  | Aberrant expression of HMGA2 | Aberrant expression of HMGA1 and A2 |

Results

UF Development in the Eker Rat Correlates with Human Disease

Figure 5:
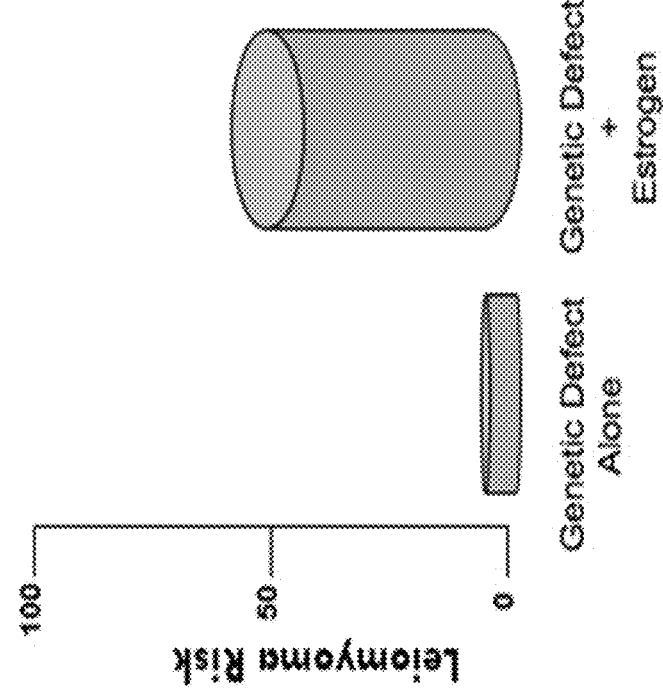
FIG. 5 is a graph of the risk of leiomyoma in Eker rats in the absence or presence of an estrogen treatment.

Eker rats harbor a germline insertion in the tuberous sclerosis 2 (Tsc2) gene that leads to its inactivation. Sixty percent of Eker rats carrying the TSC2 gene defect develop hormone-dependent UFs as shown in FIG. 5. Eker rats are therefore used as a model for human UF and related diseases. The availability of estrogen-responsive uterine fibroid-derived cell lines combined with the fact that spontaneous tumors develop with high frequency in female Eker rats has made this an animal model extremely useful for studies on uterine fibroids as shown in Table 1. Moreover, this model has the advantage to characterize the gene and environment interaction. Eker rats carrying a germline mutation in the tuberous sclerosis 2 (Tsc2) tumor suppressor gene spontaneously develop uterine fibroids with a frequency of 65% between ages 12 and 16 months. However, an early-life exposure to endocrine-disrupting chemicals such as diethylstilbestrol during the development of the uterus increases tumor-suppressor-gene penetrance to >90% and tumor multiplicity and size in genetically predisposed animals.

Figure 6A:
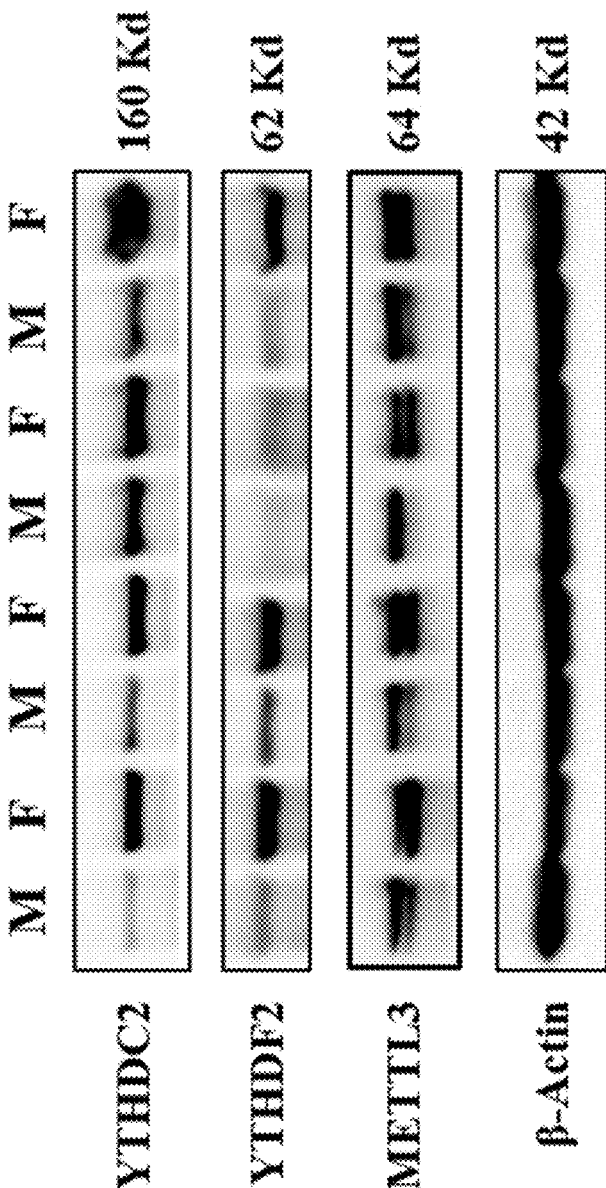
FIGS. 6A-6B are a Western blot image of METTL3, YTHDC2, and YT521-B homology domain N6-methyladenosine RNA binding protein 2 (YTHDF2) and β actin levels in UFs (F) and MyoF (M) tissue of late adult stage Eker rats (n=5) (FIG. 6A) and an immunoblot analysis dot graph of the fold change in UF over MyoF of METTL3, YTHDC2, and YTHDF2 levels (FIG. 6B). Late adult stage Eker rats are 11-15 months old.
Figure 6B:
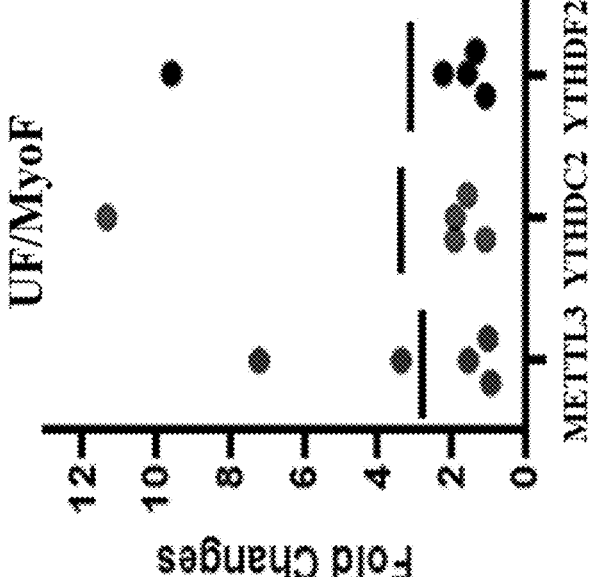
Figure 7:
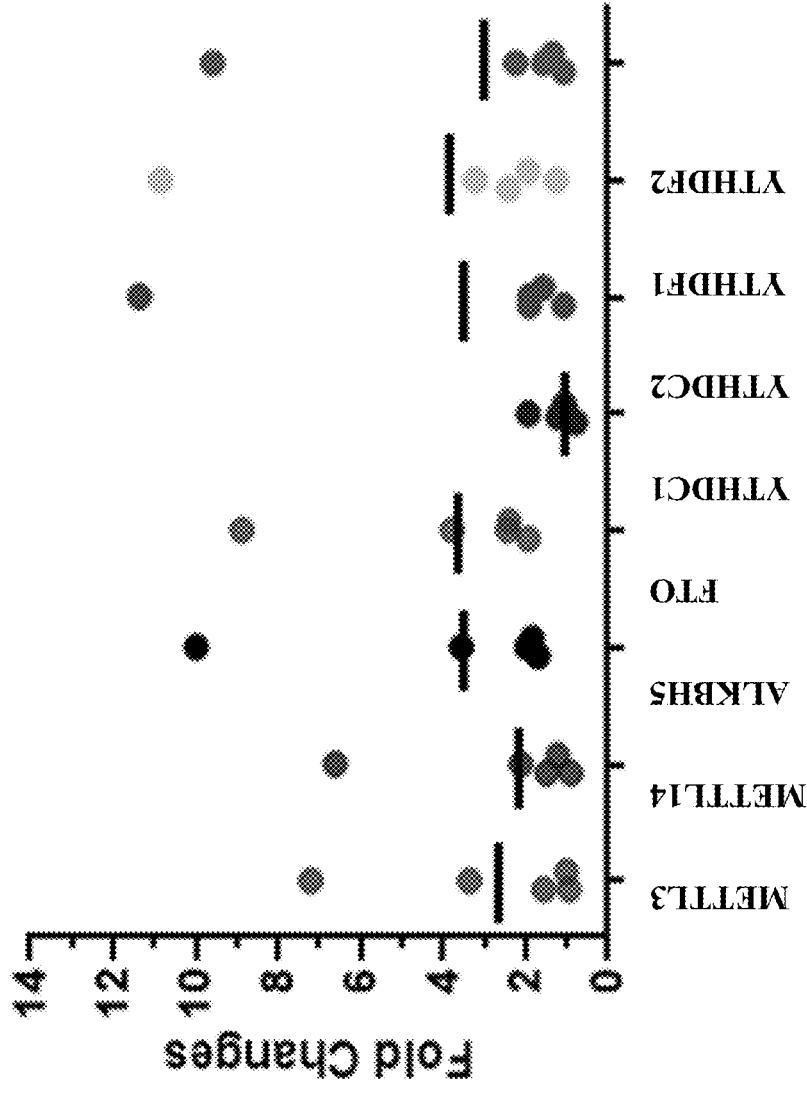
FIG. 7 is a quantitative PCR analysis dot graph showing fold change of UF (n=5) over MyoF (n=5) expression level of the m6A regulators METTL3, methyltransferase-like protein 14 (METTL14), human AlkB homolog 5 (ALKBH5), fat mass and obesity-associated protein (FTO), YT521-B homology domain containing protein 1 (YTHDC1), YTHDC2, YT521-B homology domain N6-methyladenosine RNA binding protein 1 (YTHDF1), and YTHDF2 in Eker rats.

Eker rat UFs and adjacent MyoF tissues were collected at the late adult stage. The expression levels of METTL3, YTHDC2, and YTHDF2 are upregulated in UFs compared to matched MyoF in Eker rats, as shown in FIGS. 6A-B. Quantitative PCR was performed to determine the RNA expression of eight m6A regulators. As shown in FIG. 7, the expression levels of M6A regulators including METTL3, METTL14, ALKBH5, FTO, YTHDC2, YTHDF1, and YTHDF2 are upregulated in UFs as compared to matched MyoF tissues in Eker rats.

These results demonstrate that m6A writer METTL3 protein is aberrantly expressed in UFs from human and Eker rats. In addition to METTL3, other m6A regulators are also dysregulated in UFs from both human and Eker rats compared to matched MyoF tissues.

Example 3

This example demonstrates inhibiting m6A regulators decrease the proliferation of UF cells.

Materials and Methods

Cell Culture

The HuLM cell line was cultured and maintained in phenol red-free, Dulbecco's Modified Eagle Medium: Nutrient Mixture F-12. The cells were grown at 37° C. and 5% $CO_2$ in an incubator with saturating humidity.

Cell Proliferation Assay of METTL3 Inhibition

Cell proliferation was measured using trypan blue exclusion assay. The cells were cultured in the absence or presence of the METTL3 inhibitor STM2457 at a dose range from 1-10 μM for 24 hours. DMSO was used as a vehicle control. Cells were trypsinized, collected by centrifuge, and resuspended in serum-free medium. Equal volumes of 0.4% trypan blue and cell suspension were mixed and cells were counted using a hemacytometer. This assay was performed three times in triplicate.

Results

Figures 8A, 8B:
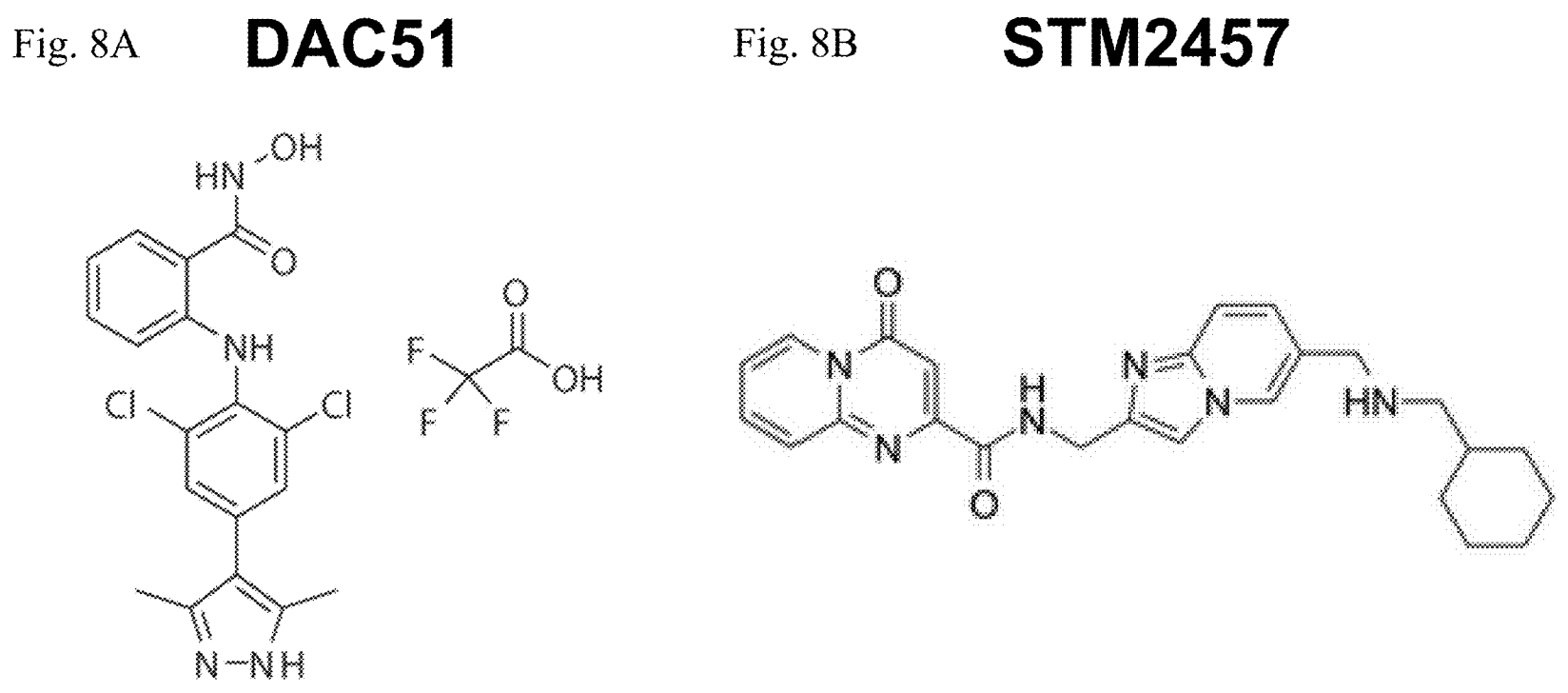
Figure 9:
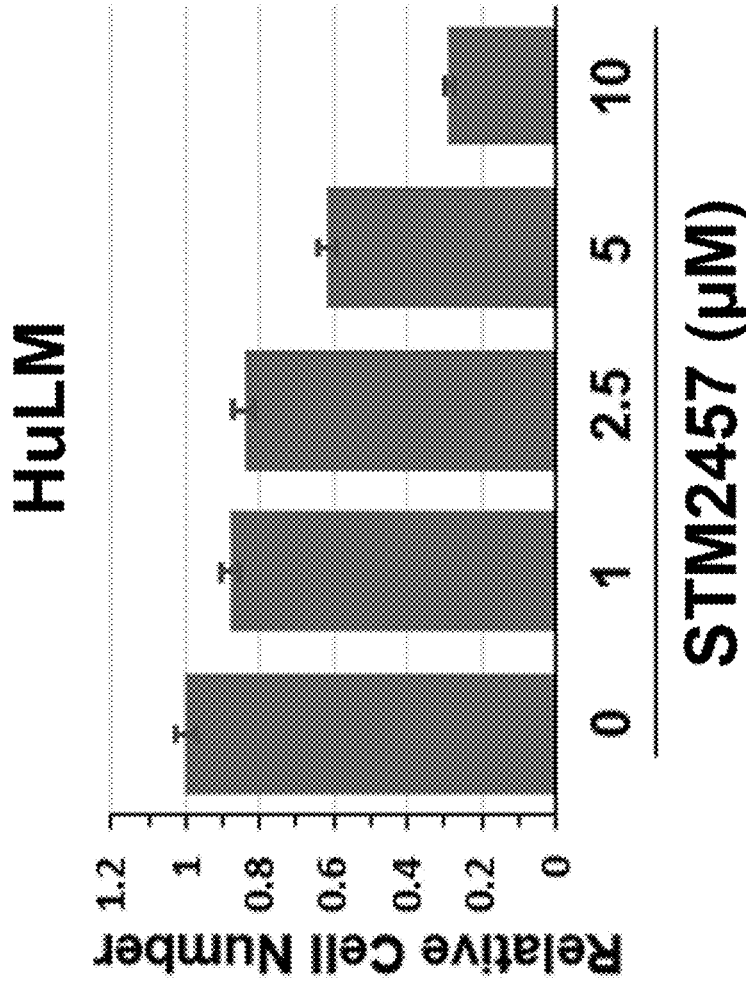
FIG. 9 is a cell proliferation bar graph showing the relative cell numbers in the absence or presence of the METTL3 inhibitor, STM2457, at concentrations between 0-10 µM, in HuLM cells.

Inhibiting the m6A writer METTL3 using STM2457 (FIG. 8B) decreases the cell proliferation of UF cells as shown in FIG. 9.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred aspects of this invention are described herein, including the best mode known to the inventors for carrying out the invention. Variations of those preferred aspects may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A method of treating a uterine fibroid in a female mammal, the method comprising administering to the female mammal an effective amount of an agent that inhibits an N6-methyladenosine (m6A) regulator, wherein the m6A regulator is an m6A writer, and wherein the agent is STM2457.

2. A method of treating a uterine fibroid in a female mammal, the method comprising administering to the female mammal an effective amount of an agent that inhibits an N6-methyladenosine (m6A) regulator, wherein the m6A regulator is an m6A writer, wherein the agent is a lentivirus, wherein the m6A writer is methyltransferase-like 3 (METTL3), wherein the lentivirus knocks down the METTL3, and wherein the lentivirus is a shMETTL3 lentivirus.

* * * * *